United States Patent [19]

Hyman

[11] Patent Number: 5,516,664
[45] Date of Patent: May 14, 1996

[54] ENZYMATIC SYNTHESIS OF REPEAT REGIONS OF OLIGONUCLEOTIDES

[76] Inventor: Edward D. Hyman, 2100 Sawmill Rd. Apt. 4-103, River Ridge, La. 70123

[21] Appl. No.: 161,224

[22] Filed: Dec. 2, 1993

Related U.S. Application Data

[63] Continuation-in-part of Ser. No. 100,671, Jul. 30, 1993, which is a continuation-in-part of Ser. No. 995,791, Dec. 23, 1992, Pat. No. 5,436,143.

[51] Int. Cl.$^6$ .............................. C12P 19/34; C07H 21/00
[52] U.S. Cl. .................. 435/91.52; 435/91.1; 435/91.3; 435/91.5; 435/91.53; 536/25.3; 536/25.31; 935/17
[58] Field of Search .................. 435/91.1, 91.3, 435/91.5, 91.52, 91.53; 536/25.3, 25.31; 935/17

[56] References Cited

U.S. PATENT DOCUMENTS

| | | | |
|---|---|---|---|
| 3,850,749 | 11/1974 | Kaufmann et al. | 435/91.3 |
| 4,661,450 | 4/1987 | Kempe et al. | 435/172.3 |
| 4,987,071 | 1/1991 | Cech et al. | 435/91.1 |

OTHER PUBLICATIONS

Cameron et al, Biochem. 16(23): 5120–5126 (1977).
Shum et al., "Simplified method for large scale enzymatic synthesis of oligoribonucleotides", Nucleic Acids Res. 5: 2297–2311 (1978).
Schott et al., "Single–step elogation of oligodeoxynucleotides using terminal deoxynucleotidyl transferase", Eur. J. Biochem. 143: 613–620 (1984).
Mackey et al., "New approach to the synthesis of polyribonucleotides of defined sequence", Nature 233: 551–553 (1971).
Hinton et al., "The preparative synthesis of oligodeoxy–ribonucleotides using RNA ligase", Nucleic Acids Res. 10: 1877–1894 (1982).
England et al., "Dinucleotide pyrophosphates are substrates for T4–induced RNA ligase", Proc. Nat'l Acad Sci. (USA) 74: 4839–4842 (1977).
Beckett et al., "Enzymatic Synthesis of Oligoribonucleotides", in *Oligonucleotide Synthesis: A Practical Approach*, M. J. Gait ed., pp. 185–197 (1984).
Mudrakovskaya et al., "RNA Ligase of Bacteriophage T4. VII: A solid pahse enymatic synthesis of oligoribonucleotides", Biorg. Khim., 17: 819–822 (1991).
Stuart et al., "Synthesis and Properties of Oligodeoxynucleotides with an AP site at a preselected location", Nucleic Acids Res. 15: 7451–7462 (1987).
Norton et al., "A ribonuclease specific for 2'–O–Methyltaed Ribonulceic Acid", J. Biol. Chem. 242: 2029–2034 (1967).
Eckstein et al., "Phosphorothioates in molecular biology", TIBS 14:97–100 (1989).
Bryant et al., "Phosphorothioate Substrates for T4 RNA Ligase", Biochemistry 21: 5877–5885 (1982).
McLaughlin et al., "Donor Activation in the T$ RNA Ligase Reaction", Biochemistry 24: 267–273 (1985).

Ohtsuka et al., "A new method for 3'–labelling of polyribonucleotides by phosphorylation with RNA ligase and its aplication to the 3'–modification for joining reactions", Nulceic Acids Res. 6: 443–454 (1979).
Kornberg, A., "Reversible Enzymatic Sysnthesis of Diphosphopyridine nucleotide and inorganic pyrophosphate", J Biol. Chem. 182: 779–793 (1950).
Kaplan et al., "Enzymatic Deamination of Adenosine Derivatives", J. Biol. Chem. 194: 579–591 (1952).
Bartkiewicz et al., "Nucleotide pyrophosphatase form potato tubers", Eur. J. Biochem. 143: 419–426 (1984).
Rand et al., "Sequence and cloning of bacteriophage T4 gene 63 encoding RNA ligase and tail fibre attachment activities", The EMBO Journal 3: 397–402 (1984).
Heaphy et al., "Effect of Single Amino Acid Chnages in the Region of the Adenylation Site of T4 RNA llgase", Biochemistry 26: 1688–1696 (1987).
Lowe et al., "Molecular cloning and expression of a cDNA encoding the membrane–associated rat intestinal alkaline phosphatase", Biochem. Biophys. Acta 1037: 170–177 (1990).
Chang et al., "Molecular Biology of Terminal Transferase", CRC Crit. Rev. Biochem. 21: 27–52.
Razzell et al., "Studies on POlynucleotides: III. Enzymatic Degaradtion. Substrate Specificity and Properties of Snake Venom Phosphodiesterase", J. Biol. Chem. 234: 2105–2113 (1959).
Tessier et al., "Ligation of Single–Stranded Oligodeoxyribonucleotides by T4 RNA Ligase", Analytical Biochemistry 158: 171–178 (1986).
England et al., "Enzymatic Oligoribonucleotide Synthesis with T4 RNA Ligase", Biochemistry 17: 2069–2076 (1978).

(List continued on next page.)

*Primary Examiner*—David M. Naff
*Assistant Examiner*—Francisco C. Prats
*Attorney, Agent, or Firm*—Oppedahl & Larson

[57] ABSTRACT

Enzymatic synthesis of a repeat region of an oligonucleotide may be performed by the steps of: (a) combining a primer and a blocked nucleotide in the presence of a chain extending enzyme whereby a primer-blocked nucleotide product is formed containing the blocked nucleotide coupled to the primer at its 3'-end; (b) removing the blocking group from the 3'-end of the primer-blocked nucleotide product using a 3'-phosphatase enzyme substantially without removing the 3'-phosphate blocking group from unreacted 3'-phosphate-blocked nucleotide; and (c) repeating the cycle of steps (a) and (b), using the primer-nucleotide product of step (b) as the primer for step (a) in the next cycle, for sufficient cycles to form the oligonucleotide product. These cycles are performed preferably in a single vessel without intermediate purification of oligonucleotide product.

Also disclosed is a process for synthesizing an oligonucleotide having a defined sequence including at least one repeat region and one non-repeating region, wherein at least one non-repeating region is synthesized by reaction cycles using the steps of extending a primer with a 3'-blocked nucleotide, inactivating unreacted 3'-blocked nucleotide, and removing the blocking group from the extended primer. The disclosed processes may be used to synthesize repeat regions of oligoribonucleotides.

21 Claims, 5 Drawing Sheets

OTHER PUBLICATIONS

Middleton et al., "Synthesis and Purification of Oligonucleotides Using T4 RNA Ligase and Reverse–Phase Chromatography", Analytical Biochemistry 144: 110–117 (1985).

Uhlenbeck et al. "T4 RNA Ligase", The Enzymes XV: 31–58 (1982).

Hoffman et al. "Synthesis and reactivity of intermediates formed in the T4 RNA ligase reaction", Nucleic Acids Res. 15: 5289–5301 (1987).

Soltis et al., "Independent Locations of Kinase and 3'–Phosphatase Activities on T4 Polynucleotide Kinase", J. Biol. Chem. 257: 11340–11345 (1982).

Apostol et al., "Deletion Analysis of a Multifunctional Yeast tRNA Ligase Polypeptide", J. Biol. Chem/ 266: 7445–7455 (1991).

Becker et al., "The Enzymatic Cleavage of Phospahte Termini from Polynucleotides", J. Biol. Chem. 242: 936–950 (1967).

Greer et al., "RNA Ligase in Bacteria: Formation of a 2', 5' Linkage by an *E. Coli* Extract", Cell 33: 899–906 (1983).

Schwartz et al., "Enzymatic Mechanism of an RNA Ligase from Wheat Germ", J. Biol. Chem. 258: 8374–8383 (1983).

BASIC MODE primer + AppNp

↓ RNA ligase incubation, then heat inactivate primer-pNp + AppNp + AMP

↓ 3' Phosphatase Incubation, then heat inactivate primer-pN + AppNp + AMP + $PO_4$ ↓ Repeat cycle until oligonucleotide substrate has been added to primer the desired number of times

PREFERRED MODE primer + AppNp

↓ RNA ligase incubation, heat inactivation optional primer-pNp + AppNp + AMP

↓ Exonuclease incubation, then heat inactivate Exonuclease and RNA Ligase primer-pNp + AppNp + AMP ↓ 3' Phosphatase Incubation, then heat inactivate primer-pN + AppNp + AMP + $PO_4$ ↓ Repeat cycle until oligonucleotide substrate has been added to primer the desired number of times

ENZYMATIC SYNTHESIS OF REPEAT REGIONS OF OLIGONUCLEOTIDES

SPECIFICATION

This application is a continuation-in-part of copending U.S. patent application Ser. No. 08/100,671, filed Jul. 30, 1993, which is a continuation-in-part of copending U.S. patent application Ser. No. 07/995,791, filed Dec. 23, 1992, now U.S. Pat. No. 5,436,143, both of which are incorporated herein by reference.

BACKGROUND OF THE INVENTION

Synthetic oligonucleotides play a pivotal role in molecular biology research, useful especially for DNA sequencing, DNA amplification, and hybridization. A novel method for the synthesis of oligonucleotides has been described previously by the inventor in U.S. patent applications Ser. Nos. 07/995,791 and 08/100,671 to replace both the obsolete enzymatic methods and the current chemical methods. This method, referred to herein as the "One Pot" method basically involves repeated cycles of extending a primer chain using a nucleotide having a 3'-blocking group, thus forming an extended primer with a blocking group at its 3'-end; inactivation of excess nucleotide; and removal of the 3'-blocking group from the extended primer to prepare the extended primer for the addition of the next nucleotide. The ease with which this method can be automated will foster a new generation of oligonucleotide synthesizers with enormous throughput, increased reliability, lower cost per synthesis, and with environmentally friendly reagents.

One limitation associated with the One Pot method previously described, however, is the inactivation of the nucleotide substrate in each cycle so that it will not interfere in subsequent cycles of the synthesis. Nucleotide substrate inactivation is necessary if a different base is to be added in the next cycle. However, if the same base is to be added in the next cycle, then it would be desirable to be able to skip the inactivation step and utilize the unincorporated nucleotide substrate in the next cycle, and perhaps several more ensuing cycles. No previous method exists, however, in which nucleotide substrate is reused, with or without intermediate purification. It is an object of the present invention to provide such a method.

The challenge presented by this objective is evident when it is considered that the same blocking group exists, in substantially similar chemical environments, on the 3'-end of the extended primer and on the 3'-end of unincorporated nucleotides, and that removal of the blocking group from the extended primer must be accomplished selectively, i.e., without substantial removal of the blocking group from unincorporated nucleotide substrate. Nevertheless, a successful approach has been devised which permits the selective removal of the blocking group from the primer-blocked nucleotide product, without removing the blocking group from and thus inactivating the nucleotide substrate. As a result, an oligonucleotide synthesis can be performed with less nucleotide substrate reagent consumption, and therefore, at a lower cost.

SUMMARY OF THE INVENTION

In accordance with the invention, there is provided a method for enzymatic synthesis of oligonucleotides having a defined sequence that includes at least one repeat region in which a repeated nucleotide occurs more than once in succession. The repeat region is formed by the step of (a) enzymatically coupling an oligonucleotide primer with a 3'-phosphate-blocked repeated nucleotide to form a 3'-phosphate blocked primer; and (b) removing the 3'-blocking group from the 3'-phosphate-blocked primer using a 3'-phosphatase enzyme substantially without removing the 3'-phosphate blocking group from unreacted 3'-phosphate-blocked repeated nucleotide. Steps (a) and (b) are then repeated one or more times using unreacted 3'-phosphate-blocked repeated nucleotide from step (b) as the 3'-phosphate-blocked nucleotide of step (a) and the deblocked primer product of step (b) as the oligonucleotide primer of step (a) to form the repeat region.

This method is advantageously performed in a single vessel without intermediate purification of oligonucleotide product and preferably without replenishment of the blocked nucleotide substrate. The removal of the blocking group is preferably performed using an enzyme, particularly 3'-phosphatase.

In accordance with one embodiment of the invention, a single cycle of the method consists of the steps in sequence:

(a) incubation of an oligonucleotide primer with RNA Ligase and AppNp or precursors thereof, wherein Np represents a nucleotide having a phosphate blocking group at the 3'-end;

(b) heat inactivation of RNA Ligase;

(c) incubation with 3'-Phosphatase to remove the phosphate blocking group; and (d) heat inactivation of 3'-Phosphatase.

In accordance with a preferred embodiment, a single cycle of the method consists of the steps in sequence:

(a) incubation of an oligonucleotide primer with RNA Ligase and AppNp;

(b) incubation with an Exonuclease (e.g. Polynucleotide Phosphorylase);

(c) heat inactivation of the Exonuclease and RNA Ligase;

(d) incubation with 3'-Phosphatase; and (e) heat inactivation of 3'-Phosphatase.

The present invention complements the One Pot method, previously described by the inventor to synthesize any oligonucleotide. Cycles of the method of the present invention may be used to synthesize regions of an oligonucleotide which contain successive repeats of the same base, in combination with cycles of the previously described One Pot method to synthesize repeating or non-repeating regions of an oligonucleotide. When the blocked nucleotide used in a given cycle is not to be reused in the next cycle, then the given cycle is performed with inactivation of unreacted blocked nucleotide and favorably with removal of the blocking group from unreacted blocked nucleotide. When the blocked nucleotide used in a given cycle is to be reused in the next cycle, then the given cycle is performed without removal of the blocking group from unreacted blocked nucleotide and favorably without inactivation of unreacted blocked nucleotide. These cycles are performed preferably in a single vessel without intermediate purification of oligonucleotide product.

DETAILED DESCRIPTION OF THE INVENTION

This invention is a modification of and an improvement on the One Pot method described in the inventor's prior applications noted above. The One Pot method involves the basic steps of (1) adding a blocked nucleotide substrate to the 3'-end of a primer using a chain extending enzyme;

(2) inactivating unreacted blocked nucleotide substrate to render it substantially unreactive as a substrate for the chain extending enzyme; and (3) removing the blocking group from the 3'-end of the primer. These steps are repeated for as many cycles as necessary to arrive at a desired oligonucleotide structure.

Frequently, however, an oligonucleotide which one wishes to synthesize will contain a consecutive repeat of the same base. This base may be repeated consecutively once or it may be repeated consecutively many times. For example, the 8-mer oligonucleotide 5'-AGUGGCCC-3' contains a consecutive repeat of G and two consecutive repeats of C. Synthesizing this oligonucleotide using the basic steps of the One Pot method results in a significant waste of materials. Thus, in this situation it may be preferable when synthesizing the oligonucleotide not to inactivate or deblock the unreacted nucleotide substrate during a cycle, so that the unreacted nucleotide can be reused in the ensuing cycle. The technical challenge of such a strategy is that it entails selective removal of the blocking group from the primer without removal of the blocking group from the nucleotide substrate.

In the method of the invention using RNA Ligase as chain extending enzyme and AppNp as nucleotide substrate, the technical difficulty is more clearly defined as finding a means for selectively removing the 3'-phosphate blocking group of the extended primer, primer-pN-3'-phosphate, without removing the 3'-phosphate of the nucleotide substrate Ap-pN-3'-phosphate. This difficulty is exacerbated by the fact that primer-pN-3'-phosphate and Ap-pN-3'-phosphate are structurally identical with respect to the 3'-phosphate group in that they both share the same pN-3'-phosphate unit; the structural difference lies in a region distant from the 3'-phosphate—the component connected to the 5'-phosphate. This high degree of structural similarity would seemingly make discriminating between the substrates unachievable. Furthermore, the degree of discrimination (selectivity) must be sufficiently high to make a nucleotide substrate reuse technique useful.

In the present invention, this challenge is solved as a result of the discovery that the enzyme 3'-Phosphatase is capable of achieving the selective dephosphorylation and that it does so in a manner which makes the invention useful. Thus, in accordance with the invention, repeat regions of oligonucleotides are synthesized by adding a first 3'-phosphate-blocked repeated nucleotide to the end of a primer using a chain extending enzyme. This results in an extended primer having a phosphate blocking group at the 3'-end. This phosphate blocking group is then selectively removed from the 3'-end of the extended primer, without significantly inactivating or unblocking unreacted nucleotide in the reaction mixture. The unblocked primer is then used as the primer for a subsequent cycle or cycles, adding additional nucleotide(s) from the remaining pool of 3'-phosphate blocked nucleotides until the repeat region is complete.

As used herein, the term "3'-phosphate-blocked nucleotide" refers to nucleotides in which the hydroxyl group at the 3'-position is blocked by the presence of a phosphate at the 2'- or 3'-position which can be removed using a 3'-phosphatase. Non-limiting examples of 3'-phosphate-blocked nucleotides in accordance with the invention are nucleotidyl-3'-phosphate monoester, nucleotidyl-2',3'-cyclic phosphate, nucleotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not present dephosphorylation by 3'-phosphatase. Structures which are equivalent to phosphate, such as sulfate, can also be used, subject to the same requirement that they re removable by 3'-phosphatase.

3'-Phosphatase is able to dephosphorylate AppNp substrate, where AppNp is adenosyl diphosphate coupled to a 3'-phosphate-blocked nucleotide. The key to the present invention, however, is the previously unrecognized difference in the activity of 3'-Phosphatase on the substrates AppNp versus primer-pNp. It has been found that this difference in activity is sufficiently great that substantially all primer-pN-3'-phosphate can be dephosphorylated without substantially dephosphorylating AppNp substrate. Such a differential dephosphorylation is achieved by carefully controlling the reaction conditions, such as temperature, buffer composition, 3'-Phosphatase enzyme concentration, and duration of incubation.

Although AppNp is the preferred blocked nucleotide substrate for the present invention, any substrate may be employed provided it can be coupled to the primer by the chain extending enzyme. For example, if RNA Ligase or Transfer RNA Ligase is the chain extending enzyme, suitable substrates may include: modified AppNp in which the adenine has been modified methylated or replacement of carbon with nitrogen or nitrogen with carbon; modified AppNp in which one or more of the ribose groups has been modified by methylation, phosphorylation or deoxygenation, or by replacement of ring oxygen with nitrogen; modified AppNp in which the internucleotidic region has been modified by replacing an oxygen with sulfur, nitrogen or carbon, or by replacement of a phosphorus with sulfur. In addition, the base N in AppNp may be any of the numerous synthetic bases known provided it is compatible with the chain extending enzyme, and is not limited to uridine, cytidine, adenosine and guanidine.

It will be recognized that absolute substrate selectivity of 3'-Phosphatase is not necessary for usefulness in the invention. For example, if a high concentration of 3'-Phosphatase is used to ensure complete dephosphorylation of the primer-pN-3'-phosphate, then a small amount of AppNp may be dephosphorylated to AppN by 3'-Phosphatase. However, AppN is a substantially inactivated substrate and would represent a small fraction of the total AppNp pool.

Two 3'-Phosphatases are commercially available, bacteriophage T4 and rye grass; and both are useful in the method of the invention. The T4 enzyme is a bifunctional enzyme containing Polynucleotide Kinase and 3'-Phosphatase activities, catalyzed from two independent active sites. The T4 enzyme is commonly sold as "Polynucleotide Kinase". Since it is the 3'-phosphatase activity which is of main relevance in this invention, this enzyme herein will be referred to as T4 3'-Phosphatase. 3'-Phosphatase derived from rye grass is sold commercially as "3'-Nucleotidase" (Sigma Chemical, E.C. 3.1.3.6).

As used herein, the term "3'-phosphatase" encompasses these two enzymes, and other homologous enzymes or enzymes which perform the same function. Given that 3'-Phosphatase is probably widespread in nature, it is anticipated that other 3'-Phosphatases derived from other sources will display similar or perhaps superior selective dephosphorylation and will also be useful in the invention. Other enzymes considered 3'-phosphatases within the scope of the present invention include the yeast enzyme 2',3'-cyclicphosphatediesterase. This enzyme is one component of a three segment polypeptide and has been cloned in yeast. (Apostol et al., *J. Biol. Chem.* 266:7445–7455 (1991). The isolated cyclicphosphatediesterase has been shown to be homologous to and perform a similar RNA processing function as T4 3'-Phosphatase. The enzyme converts 2',3' cyclicphosphate nucleotides to 2'-phosphate, 3-hydroxyl nucleotides. A 2'-phosphate-3-hydroxyl primer formed using this enzyme can be extended using the ligase component of Transfer RNA Ligase which is reported to require a 2'-phosphate for extension.

Genetic mutants of T4 3'-Phosphatase which lack associated kinase activity would be useful in the invention. A genetic mutant called pseT47 and a proteolytic fragment of the enzyme have the 3'-Phosphatase activity, but no kinase activity. Soltis et al., *J. Biological Chemistry* 257: 11340–11345 (1982). Additional evidence supports the assertion that the two enzymatic activities reside in two independent active sites. Removal of the associated kinase activity may be desirable in preventing oligonucleotide circularization or polymerization as described previously. Other useful 3'-Phosphatases may be constructed by making genetic mutations which remove undesirable associated enzyme activities.

Thus far, experiments performed by the inventor have been unable to demonstrate that the invention is directly applicable for deoxyribose substrates AppdNp, since it appears that 3'-Phosphatase lacks the ability to selectively dephosphorylate primer-pdNp without substantially dephosphorylating AppdNp. Nevertheless, the synthetic method of the invention may be used for the synthesis of oligodeoxyribonucleotides by first synthesizing an appropriate oligoribonucleotide and then using it as a template for synthesis of an oligodeoxyribonucleotide in a template dependant polymerization reaction.

The method of this invention is practical because generally AppNp nucleotide substrate concentrations used in the One Pot method are substantially higher than the primer concentration in order to ensure efficient coupling. After completion of coupling, the nucleotide substrate concentration is generally still adequate to ensure efficient coupling in the ensuing cycle. Replenishment of the nucleotide substrate is generally unnecessary because only a small fraction of the substrate, 10 percent for example, is consumed by incorporation in the primer in each cycle; the remaining 90 percent nucleotide substrate is generally sufficient to ensure adequate coupling efficiency in the ensuing cycle. On the other hand, replenishment may be necessary if nucleotide substrate is only in slight molar excess over the primer concentration, or nucleotide substrate has been depleted to low levels after several consecutive reuses, or in order to ensure an adequate nucleotide substrate concentration.

In situations in which nucleotide substrate will be reused in several consecutive cycles, a higher than normal nucleotide substrate concentration may be employed in the first cycle to obviate the need for replenishment. For example, if a standard coupling protocol employs 0.10 mM primer and 1.0 mM nucleotide substrate, and the same nucleotide substrate will be added to the primer in ten consecutive cycles, a 2.0 mM nucleotide substrate concentration for the first cycle will compensate for the estimated 1.0 mM consumption of nucleotide substrate in the ten cycles. The nucleotide reuse technique saved an estimated 8 mM (10 mM–2 mM) nucleotide substrate compared with the One Pot method previously described in which unreacted nucleotide was discarded after each cycle.

The method of the invention is especially useful in synthesizing oligonucleotides or regions of oligonucleotides with numerous consecutive bases. For example, the method would be useful in adding to a primer chain a poly(A)$_{10}$ tract using the substrate AppAp, or in adding a poly(GU)$_{10}$ tract using the substrate AppGpUp, or in adding a poly(A/C)10 tract using the substrate mixture 50% AppAp+50% AppCp.

To synthesize regions of repeating nucleotides, nucleotides can also be added to the primer two at a time by using a nucleotide substrate of the formula AppN$_1$pN$_2$p where $N_1$ and $N_2$ may be the same or different. It will be appreciated, however, that the differential reactivity of the extended primer and such a substrate will be less than for the substrate AppNp. Accordingly, the selectivity of this process will be less, and the benefits in terms of materials cost will also be less.

The method of the invention can also be used in combination with addition of a further nucleotide to introduce a wobble at a selected point in the an oligonucleotide sequence. For example, if the sequence calls for addition of an A, followed by an A/G wobble, G nucleotide substrate can be simply added to the remaining A nucleotide substrate to achieve this result. The method can also be used to remove the phosphate blocking group from the extended primer in the last cycle of a synthesis, because nucleotide substrate inactivation or deblocking is generally unnecessary.

Figure 1:
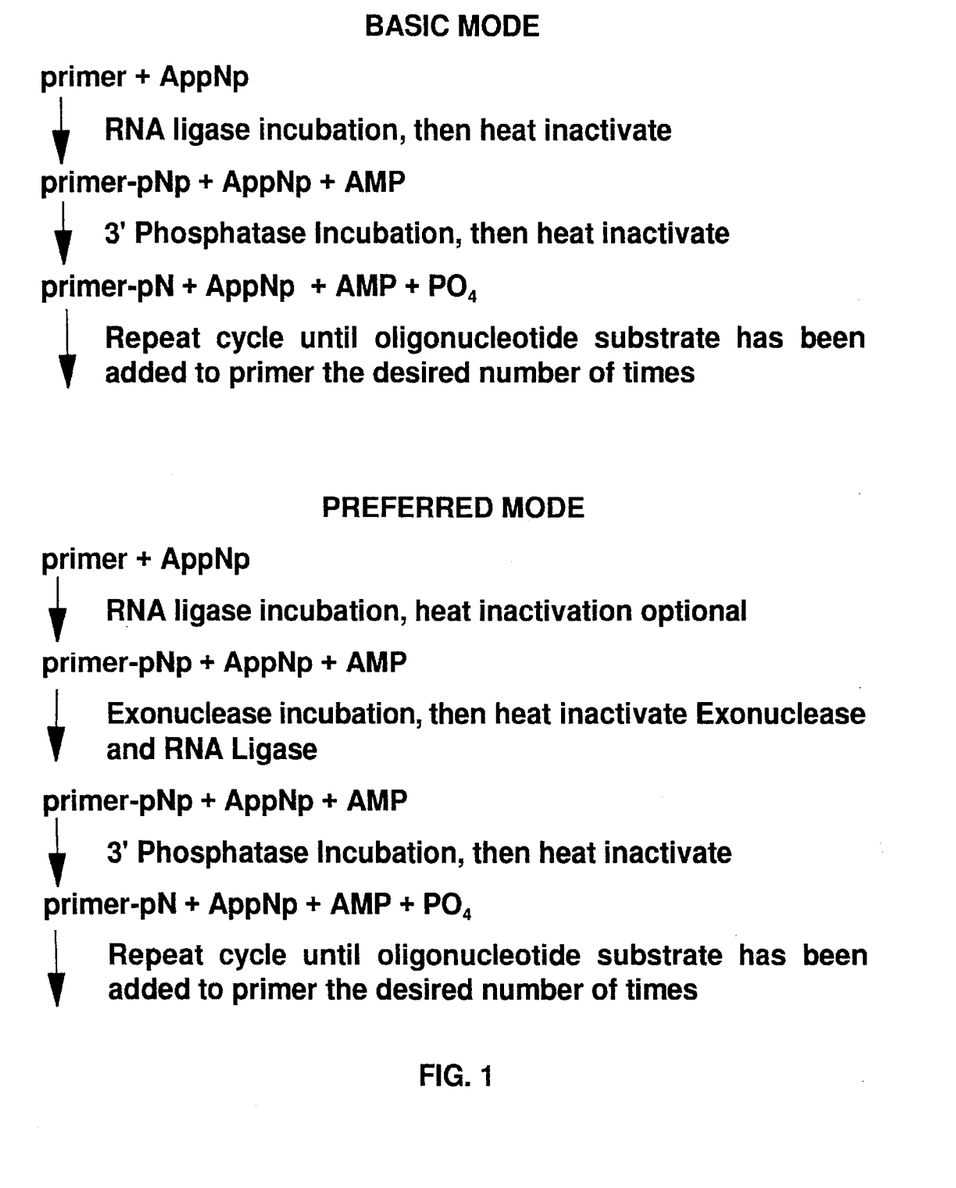
FIG. 1: Summary of Basic and Preferred modes of the One Pot method with substrate reuse.

Similar to the One Pot method, the method of the invention may be practiced in Basic or Preferred modes, summarized in FIG. 1. The Basic mode employs two steps per cycle, chain extension and primer deblocking, and is demonstrated in examples 1 and 2. The Preferred mode employs an additional step to remove unextended primer chains. This is accomplished with either an Exonuclease to hydrolyze unextended primer chains, such as Polynucleotide Phosphorylase, Exonuclease I, or Phosphodiesterase I or with a Capping Enzyme to terminate unextended chains with a chain terminating nucleotide, such as RNA Ligase and AppddN. Example 3 illustrates the Preferred mode of the invention using the Exonuclease technique. The favored technique for removing unextended primer in the Preferred mode is through the use of Polynucleotide Phosphorylase.

The use of Exonucleases in the Preferred mode of the invention requires elaboration. The Exonucleases Polynucleotide Phosphorylase and Exonuclease I do not modify AppNp substrate. In contrast, Phosphodiesterase I from snake venom inactivates AppNp substrate by converting it to AMP+3',5'-NDP. Since T4 3'-Phosphatase does not significantly dephosphorylate 3',5'-NDP during primer dephosphorylation, AppNp substrate can be reformed from 3',5'-NDP precursor in the next cycle in the presence of RNA Ligase+ATP. This allows reuse of 3',5'-NDP in the next cycle. This technique is demonstrated in example 3A. Although nucleotide substrate is inactivated by phosphodiesterase I, the blocking group is not removed from the nucleotide substrate fragment precursor, allowing reformation of nucleotide substrate in the next cycle. This example illustrates that the present invention in general can be practiced by either inactivating or not inactivating nucleotide substrate. However, the preferred practice is without nucleotide substrate inactivation or any modification, since (a) RNA Ligase coupling in the next cycle, employing precursor substrates ATP+3',5'-NDP, is slower and less efficient, and (b) ATP addition is generally necessary. Since this technique involves nucleotide substrate inactivation during a cycle, it may be classified as a variation of the One Pot method.

Inactivation of nucleotide substrate and deblocking of nucleotide substrate are separate actions, which are generally not equivalent; that is, deblocking does not necessarily inactivate, and inactivation does not necessarily deblock. The above example illustrates that inactivation of nucleotide substrate can occur without deblocking the nucleotide substrate. Conversely, deblocking of nucleotide substrate can conceivably occur without substrate inactivation. For example, if the chain extending enzyme is a mutant terminal transferase and the nucleotide substrate is dNTP-3'-phosphate, deblocking the nucleotide substrate to dNTP would not inactivate the substrate, but would probably make it more active. For the RNA Ligase chain extending enzyme with AppNp substrate, deblocking substrate to AppN also inactivates it, as previously described by the inventor.

In practicing the method of the invention, reasonable caution should be exercised to avoid significant co-incubation of RNA Ligase activity and 3'-Phosphatase activity in the presence of primer+AppNp substrates. This situation may result in uncontrolled addition of AppNp substrate to the primer, the extent of which would depend on the degree of co-incubation. What constitutes significant co-incubation is determined in the context of the end user's need for oligonucleotide product purity and yield, as the severity of the co-incubation determines the extent of detriment to product purity or yield or both. Co-incubation can be avoided in several ways.

(1) Both enzymes can be inactivated after incubation, such as by heat or by proteolytic digestion. This is the safest method for avoiding co-incubation and is the method employed in the examples at the end of the specification.

(2) Thermostable RNA Ligase could be used for coupling at high temperatures, and RNA Ligase activity could be temporarily "turned off" by lowering the temperature for subsequent incubation with 3'-Phosphatase. It is common knowledge that enzymes isolated from thermophilic organisms are usually optimally active at the temperature at which the organism grows, and that lowering the temperature can substantially lower enzyme activity. Elevating temperature would inactivate 3'-Phosphatase and "turn on" RNA Ligase activity.

(3) Thermostable 3'-Phosphatase could be used in the same manner described in (2) but using an RNA Ligase at low temperatures which is inactivated at high temperature.

(4) Conceivably, a 3'-Phosphatase may be constructed with the following characteristics: it is active at low temperature, activity can be temporarily "turned off" by increasing the temperature, and activity can be restored by lowering the temperature. Such a 3'-Phosphatase combined with an RNA Ligase as described in (2) would allow consecutive base addition by thermal cycling between high and low temperatures; one base would be added for each cycle of high and low temperature incubation.

When the 3'-phosphate blocked nucleotide is added to the end of the primer, a molecule of adenosine-5'-monophosphate (AMP) is released. To avoid any inhibition of the chain extending enzyme that may occur as a result of a build-up of AMP, it may be desirable to convert the AMP to a different form. This can be accomplished through the addition of an AMP Inactivating Enzyme or Enzyme Combination.

For the purpose of this invention, an AMP Inactivating Enzyme or Enzyme Combination is defined as an enzyme or enzyme combination which converts AMP to a less reactive form, i.e., a form which is less inhibitory to the forward coupling reaction catalyzed by RNA Ligase, or which is less able to participate in the reverse coupling reaction catalyzed by RNA Ligase, or which assists in driving (thermodynamically or kinetically) the forward coupling reaction catalyzed by RNA Ligase. An AMP Inactivating Enzyme or Enzyme Combination is useful in making the RNA Ligase coupling reaction faster, more efficient, or more reliable, by converting AMP, generated by the forward coupling reaction, to a form with diminished undesirable properties. The undesirable properties of AMP include inhibition of the forward coupling reaction and participation in the reverse coupling reaction. The enzyme 5'-Nucleotidase has previously been used by the inventor in the One Pot method as an AMP Inactivating Enzyme, by converting AMP to Adenosine. Several other AMP Inactivating Enzymes have been identified by the inventor. Similar to 5'-Nucleotidase, these new enzymes are preferably used concurrently with RNA Ligase incubation since they share the property of not substantially degrading primer, extended primer product, and App(d)Np substrate. Furthermore, similar to 5'-Nucleotidase, these enzymes can be present or can be used at any or all steps of a cycle since their activity is not deleterious to the One Sot method. Such enzymes include:

(1) AMP Nucleosidase (E.C. 3.2.2.4): AMP+$H_2O$ →Adenine+ribose-5-phosphate (2) AMP Deaminase (E.C. 3.5.4.6): AMP+$H_2O$ →Inosine-5'-phosphate+$NH_3$ Thermostable variants of these enzymes, e.g., from *Thermus aquaticus* or *Pyrococcus* may provide advantageous properties as well, because this would reduce the need to replenish the enzyme between cycles.

Figure 3:
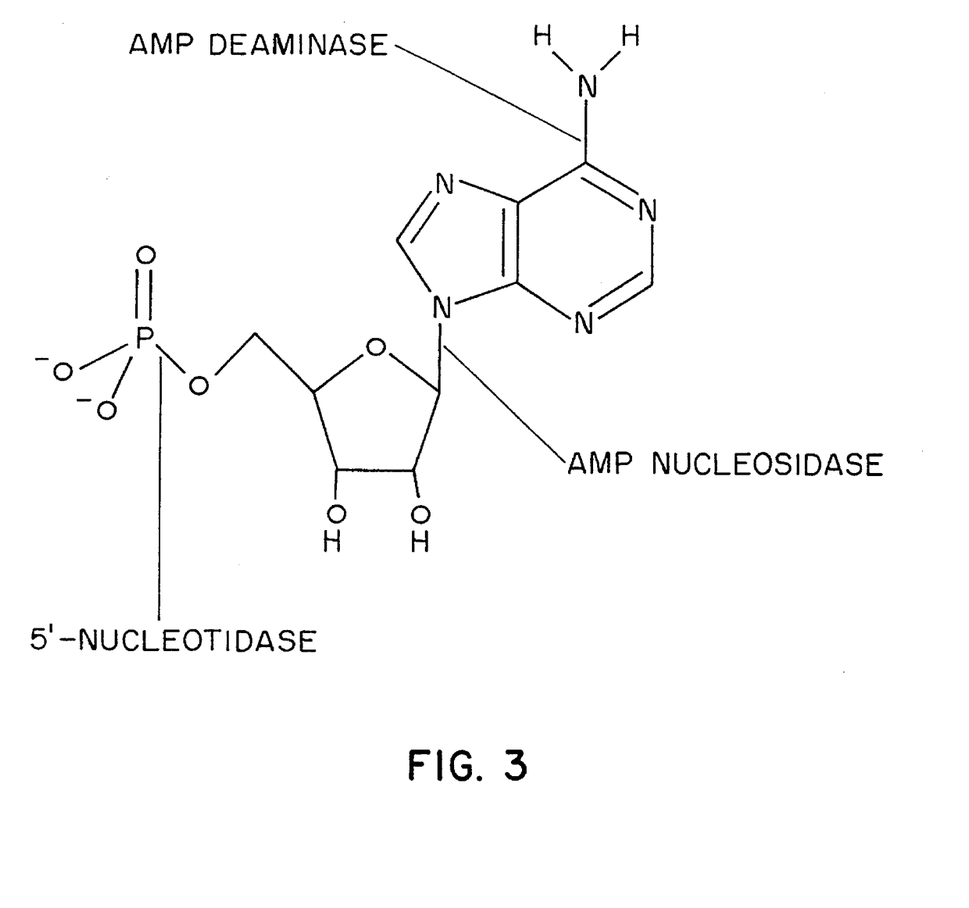
FIG. 3: Diagram of Adenosine 5'-Monophosphate (AMP) showing the location of the covalent bond broken by the hydrolytic activity of 5'-Nucleotidase, AMP Nucleosidase, and AMP Deaminase.

For clarity, FIG. 3 shows a structure of AMP and the location of the covalent bond broken by the hydrolytic activity of 5'-Nucleotidase, AMP Nucleosidase, and AMP Deaminase. Experiments by the inventor strongly suggest that the hydrolytic products of AMP Nucleosidase and AMP Deaminase are less inhibitory to RNA Ligase than AMP. Furthermore, it is believed that these hydrolytic products are unable to participate in the reverse RNA Ligase coupling reaction. Example 4 demonstrates the use of AMP Nucleosidase and AMP Deaminase.

The three enzymes using AMP substrate (5'-Nucleotidase, AMP Nucleosidase, and AMP Deaminase) may be combined in a rational manner with other enzymes, which further convert their products to even less reactive products, to create an AMP Inactivating Enzyme Combination. Such enzymes include:

(1) Adenosine Nucleosidase (E.C. 3.2.2.7): Adenosine+$H_2O$→Adenine+ribose (2) Adenosine Deaminase (E.C. 3.5.4.4): Adenosine+$H_2O$→Inosine+$NH_3$ (3) Nucleoside Phosphorylase (E.C. 2.4.2.1): Adenosine+$PO_4$→ribose-1-phosphate+Adenine (4) Uridine Nucleosidase (E.C. 3.2.2.3): Uridine+$H_2O$→Uracil+ribose Example 4 demonstrates the enzyme combination 5'-Nucleotidase +Adenosine Deaminase. Other combinations can be constructed by identifying the side product which one wishes to convert to a less reactive form and consulting *Enzyme Nomenclature* (Academic Press, 1992) or the scientific literature to locate an enzyme which effects the conversion. For example, if one wishes to remove adenine, consultation with *Enzyme Nomenclature* discloses the enzyme Adenine Deaminase (E.C. 3.5.4.2) which converts adenine to hypoxanthine, which may be suitable for inclusion in an enzyme combination.

Figure 2:
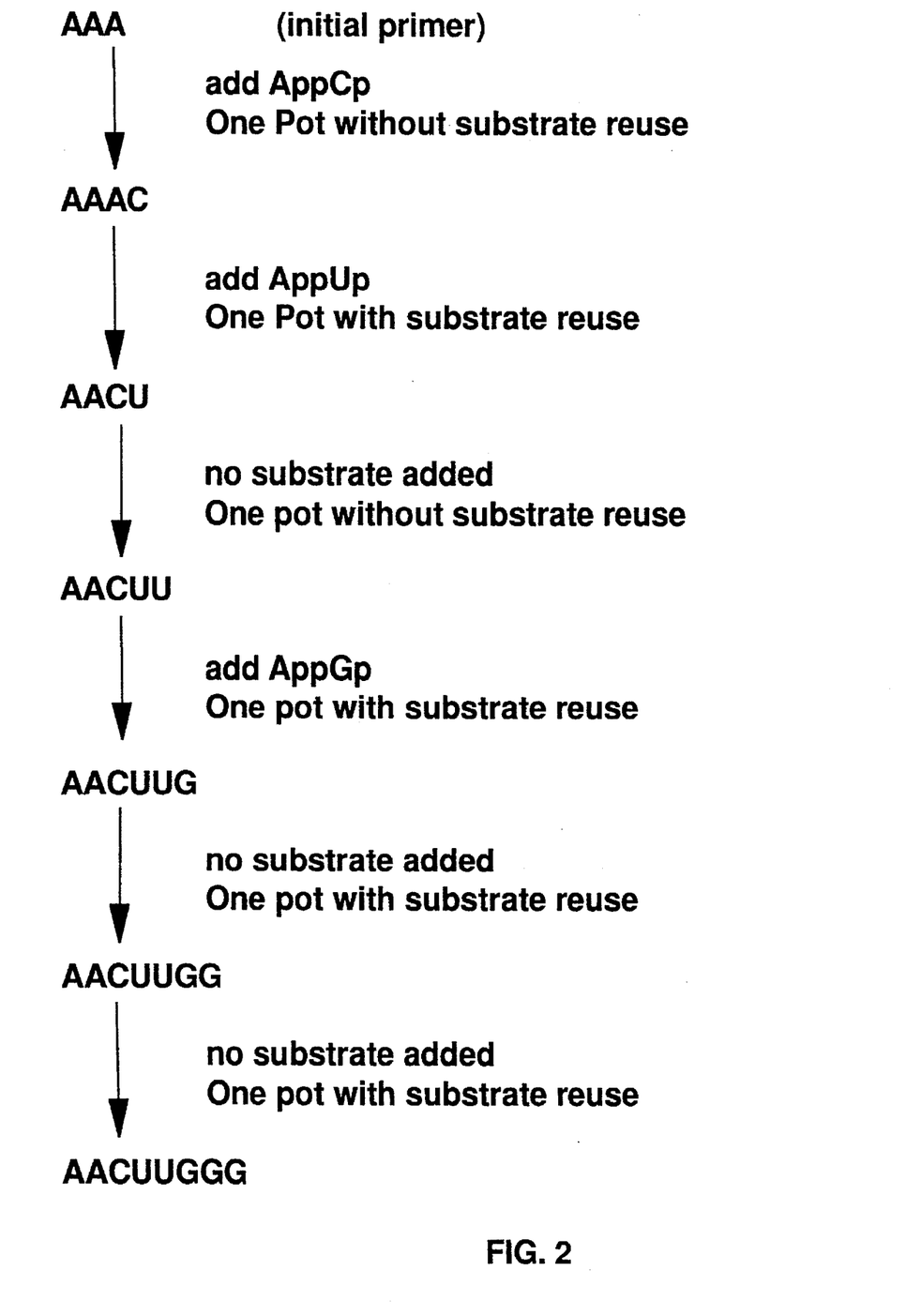
FIG. 2: Hypothetical synthesis of the 3-mer 5'-AAACU-UGGG-3' using One Pot cycles with substrate reuse and cycles without substrate reuse.

The method of the invention for synthesizing repeating regions of oligonucleotides is advantageously combined with other methods for synthesizing non-repeating regions, thus providing a method for efficient and cost effective synthesis of the complete oligonucleotide. Thus, the method of the invention may be combined with the One Pot method to yield a complete synthetic approach. FIG. 2 shows a method in accordance with the invention in which cycles of the One Pot method are used to synthesize non-repeat regions and cycles using selective phosphate removal from the primer are used to synthesize repeat regions.

The method of the invention can also be combined with other methods for synthesizing and modifying oligonucleotides, such that the One Pot method is used to make a portion of the final oligonucleotide product. Such other methods may include the blocked enzymatic method, the uncontrolled enzymatic method, the branched enzymatic method, chemical methods, transcription-based enzymatic methods, and template-based enzymatic methods. Non-limiting examples for combining the method of the invention with another method(s) are:

(1) The blocked enzymatic method may be practiced in any cycle of the One Pot method during synthesis, whereby, the oligonucleotide product is purified from all side products in this cycle. For example, a 10-mer can be synthesized by the One Pot method, purified from reaction side products by electrophoresis or chromatography, and then the purified 10-mer can be extended to a 20-mer by resumption of the One Pot method.

(2) An oligonucleotide, synthesized by in-vitro transcription or by chemical methods, may serve as the primer used in the first cycle of the One Pot method.

(3) An oligonucleotide synthesized by the One Pot method may be ligated (using RNA Ligase) to another oligonucleotide, which has been synthesized by any method, to form an oligonucleotide product. Ligation may be repeated with another oligonucleotide to form a larger oligonucleotide product. (This is the branched method).

(4) An oligonucleotide synthesized by the One Pot method can be extended enzymatically. For example, Poly(A) Polymerase+ATP can be used to add a poly(A) tail; Terminal Deoxynucleotidyl Transferase+dTTP can be used to add a poly(dT) tail; or RNA Ligase+3'-Phosphatase+AppNp can be used to add a poly[N] tail.

(5) An oligonucleotide synthesized by the One Pot method can be annealed to a template nucleic acid such that the oligonucleotide can be extended in a template dependent manner using DNA polymerase+dNTP's.

(6) An oligonucleotide synthesized in part or in whole using the One Pot method can be subsequently modified enzymatically or chemically to favorably alter its chemical properties. For example, the oligonucleotide may be phosphorylated at the 5' end with Polynucleotide Kinase. For example, an oligonucleotide synthesized by the One Pot method can be methylated using a methylating chemical reagent, to improve lipid solubility properties and resistance to nuclease digestion, for use as a therapeutic anti-sense oligonucleotide.

(7) Any combination of the above.

While the synthesis of an oligonucleotide can be effectively performed using the basic method outlined herein as amplified by the examples below, some procedures and some reagents may require that special care be taken to minimize damage to the oligonucleotide. Two potential causes of damage that may need to be considered have been described in the literature: metal catalyzed hydrolysis and free radical damage.

Metal Catalyzed RNA Hydrolysis: Although hydrolysis of RNA can occur exceedingly slowly in the absence of metal cations, numerous observations in the scientific literature report that hydrolysis is accelerated by the presence of metal cations (unrelated to hydrolysis by protein enzymes). The relative lability of RNA, versus DNA, is explained by the vicinal 2',3'-diol structure of ribose bases.

There is little direct teaching in the literature on how to inhibit metal catalyzed RNA hydrolysis; however, the following recommendations may be implemented by the researcher either to lessen the chances of this problem from occurring or to lessen the severity of this problem if it does occur.

(1) Reduce or eliminate contamination with metal cations which are not required by, or used to stimulate the activity of, the enzymes in the One Pot method, especially $Pb^{+2}$.

(2) Reduce the concentration of a metal cation(s) which are required by, or used to stimulate the activity of, an enzyme(s) in the One Pot method. For example, try lowering the $Mg^{+2}$ or $Zn^{+2}$ concentration.

(3) Add a chelator which may selectively bind problematic cations to reduce the hydrolysis rate.

(4) Reduce the duration of high temperature incubations during synthesis, especially for heat inactivations.

(5) Try lowering the pH of the synthesis reaction solution, if possible.

(6) Synthesize the oligonucleotide using nucleotide substrate analogs which may be more resistant to metal catalyzed hydrolysis. For example, phosphorothioate analogs or 2'-O-methyl analogs may eliminate this problem.

(7) After completion of synthesis, any of the following measures may be taken: (a) keep the solution chilled, or (b) add protease to the synthesis to destroy any trace RNase contamination, or (c) add an organic solvent such as phenol chloroform: 8-hydroxyquinolone.

Free Radical Damage: Free radicals can damage purine bases, pyrimidine bases, and can cleave the oligonucleotide. Free radicals are known to be generated by co-incubation of $Fe^{+2}$ (or other heavy metal cations), a thiol, and oxygen. If free radical damage becomes problematic for a given synthesis, several measures may be optionally taken: reducing solution contamination by heavy metals, decreasing thiol concentration, conducting the synthesis in an oxygen-free environment, adding chelators to inhibit free radical generation, adding free radical scavengers, or adding enzymes to consume free radicals.

The method described in this specification, favorably synthesizes oligoribonucleotides as the result of the preference of RNA Ligase for RNA primers. However, oligoribonucleotides are anticipated to readily substitute for corresponding oligodeoxyribonucleotides for most applications. Substituting an oligoribonucleotide for a oligodeoxyribonucleotide may require a slight alteration of a protocol by the knowledgeable application of enzymes with known activities, such as reverse transcriptases, RNases, DNases, RNA Ligase, DNA Ligase, exonucleases, and phosphatases, without undue experimentation. Examples of how several common applications for oligodeoxyribonucleotides may be suitably modified follow.

(1) Conversion to Complementary DNA: The oligoribonucleotide can be synthesized with a hairpin at the 3' end, allowing priming for reverse transcriptase, and subsequent RNase H digestion.

(2) DNA Sequencing by Sanger dideoxy method: No protocol modification is anticipated since the DNA polymerases used in the sequencing reactions are known to be able to use oligoribonucleotide primers. The RNA primer could be removed from the DNA by RNase prior to electrophoresis.

(3) Ligase Chain Reaction: No protocol modification is anticipated since DNA Ligases are known to also ligate RNA.

(4) Polymerase Chain Reaction: A thermostable reverse transcriptase would be needed to copy oligoribonucleotide primer ends; several such enzymes are commercially available (Amersham and Perkin-Elmer).

(5) Synthetic Gene Construction: Two techniques are conceivable: (a) Overlapping annealing oligoribonucleotides can be converted to a double stranded nucleic acid with reverse transcriptase and DNA Ligase, and subsequently amplified by polymerase chain reaction, and (b) Several oligoribonucleotides can be individually converted to double stranded DNA and ligated together.

(6) Site Directed Mutagenesis using M13: A reverse transcriptase would be necessary to convert the mutant circular single stranded DNA/RNA hybrid to double strand. The RNA region could be subsequently replaced with DNA using RNase H+DNA polymerase+DNA ligase+polynucleotide kinase before transfection.

The minimal configuration for an apparatus which is useful for synthesizing oligonucleotides by the One Pot method is: (1) at least one vessel containing reaction solution for performing the synthesis of an oligonucleotide, (2) means for controlling the temperature of the reaction solution(s), (3) means for separately supplying at least four different blocked nucleotide feed stocks to the solution(s), (4) means for supplying at least one enzyme feed stock to the solution(s), and (5) means for controlling the sequential addition of blocked nucleotide feed stocks and enzyme feed stock(s) to the solution(s). Two separate embodiments of the minimal configuration are described for synthesizing multiple oligonucleotides simultaneously or for synthesizing a single oligonucleotide in bulk.

Figure 4:
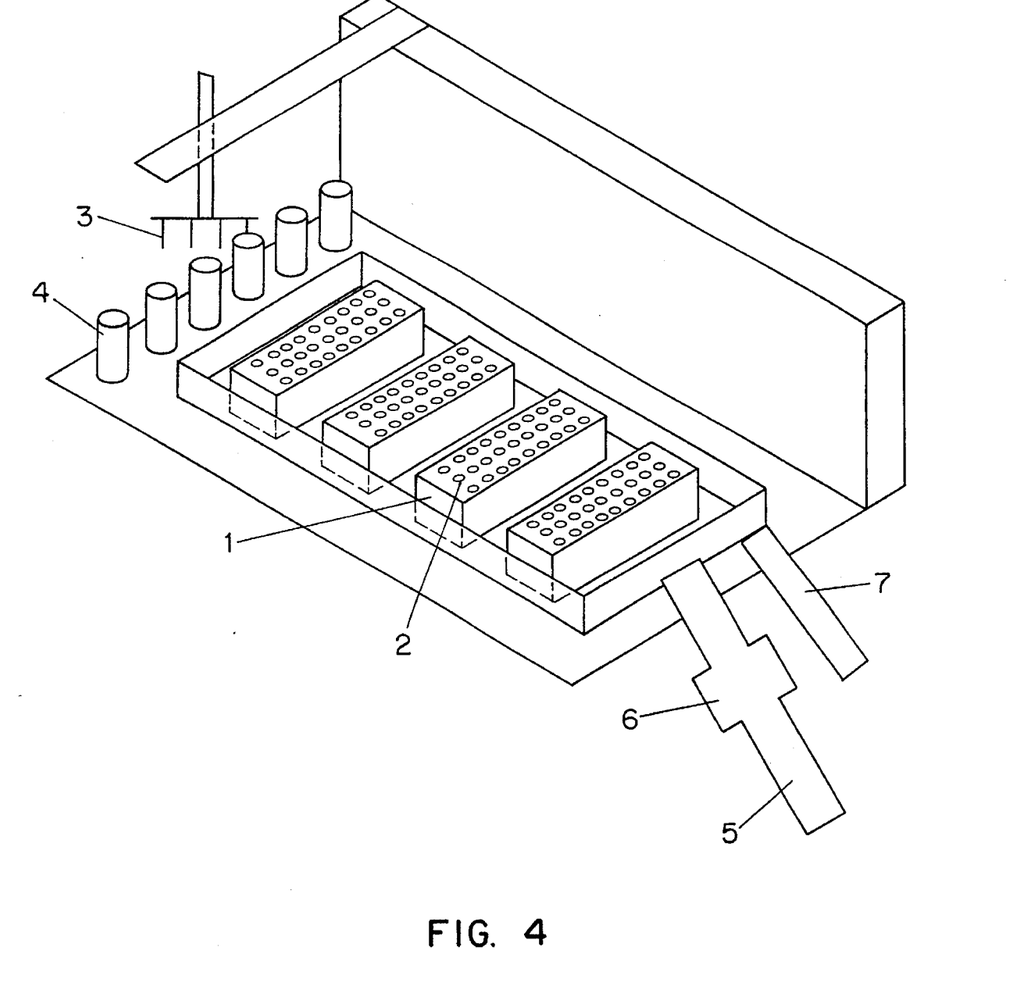
FIG. 4: Automated instrument for the simultaneous synthesis of multiple oligonucleotides using the One Pot method.

FIG. 4 shows an apparatus which can be used in the practice of the invention for synthesizing multiple oligonucleotides simultaneously. The apparatus has a plurality of reaction vessels in the form of wells 2 drilled in a metal block 1. At least four different blocked nucleotide feed stocks and at least one enzyme feed stock are provided from reagent bottles 4 using one or several liquid handling robots 3. The temperature of the block can be increased by turning on a heating element (not shown) beneath the block and can be lowered by opening a valve 6 which allows water 5 to flow through a cavity (not shown) underneath the block and then exit 7. A computer (not shown) controls the sequential addition of blocked nucleotides and enzyme(s) to the vessels and controls the temperature of the block. This apparatus is similar to the previously described apparatus, with the exception that the apparatus need not inactivate chain extending enzyme.

This apparatus can be further improved by providing a means for mixing the synthesis reaction solutions without the need for the robotic liquid dispensing system to mix reaction solutions. The robotic dispensing system is thereby dedicated mainly to adding reagents, avoiding the delay of mixing of each individual synthesis reaction. This can be accomplished by placing a magnetic stir bar in each of the wells in active use, and agitating the stir bars with a magnetic stirrer located below the wells. It can also be accomplished by placing many small magnets or paramagnetic particles in each active well and agitating these particles with a moving magnetic field.

The possibility that metal ions may leach into the synthesis reaction in amounts causing hydrolysis of RNA may warrant additional measures. The metal of the well may be inert (e.g. titanium), the surface of the well may be coated with an inert material such as TEFLON, or the synthesis reactions may be carried out in removable multi-well plastic microtiter trays. The same precautions should be considered for any component which contacts the reaction solution or the feed stocks.

Figure 5:
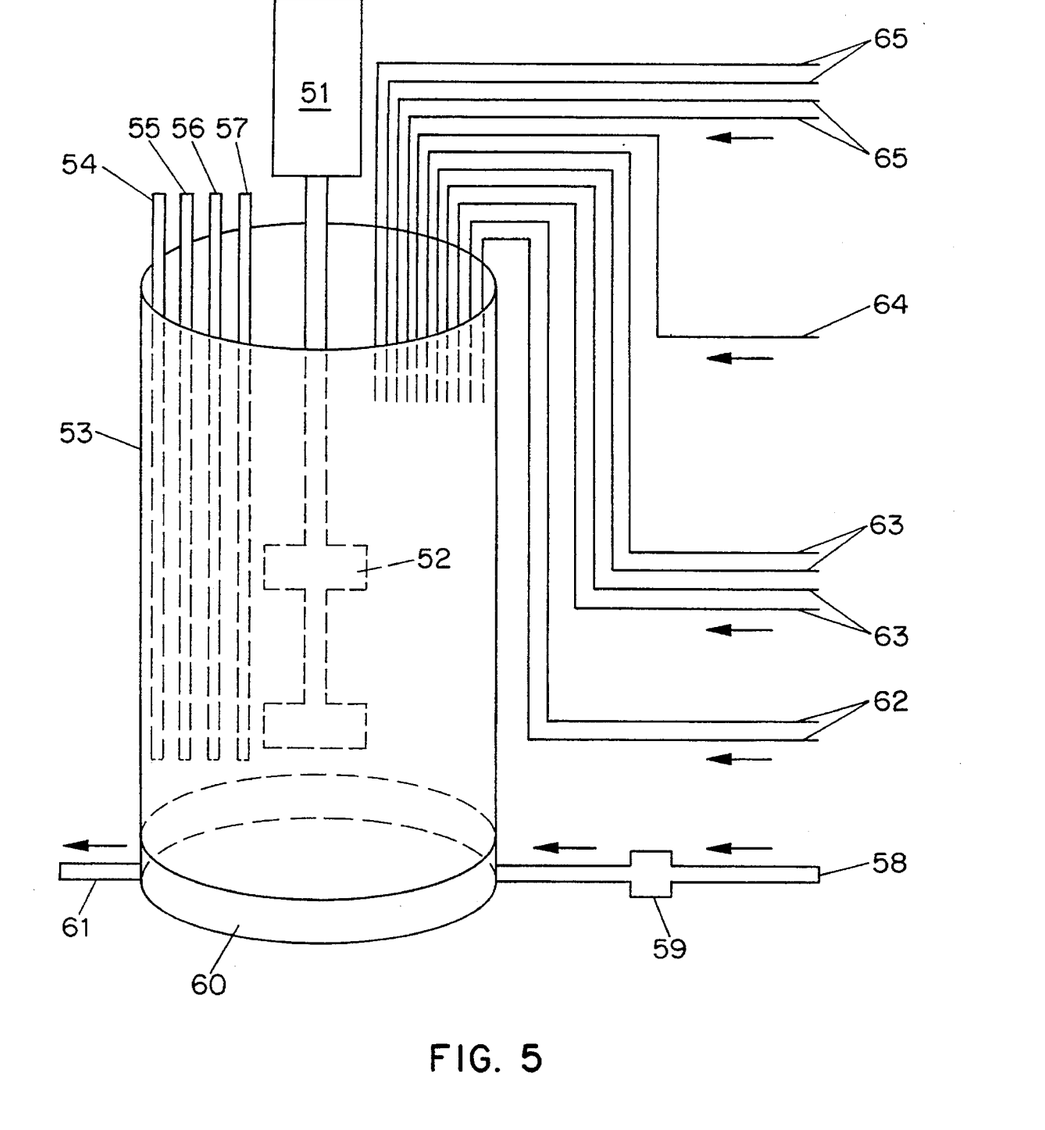
FIG. 5: Automated instrument for the large scale synthesis of one oligonucleotide using the One Pot method.

FIG. 5 shows an apparatus which can be used in the practice of the invention for synthesizing a single oligonucleotide in bulk quantity. It consists of a single large vessel 53 for the synthesis reaction which is mixed by a stirring device. The stirring device may be a motor 51 connected to a rotating impeller 52, or alternatively a large stir bar (not shown) rotated by a magnetic stirrer (not shown). The temperature of the reaction solution is increased with a heating device 54 or a heating element (not shown) located inside cavity 60, and lowered by opening a valve 59 which allows cool water 58 to flow into a cavity 60 beneath the vessel and then exit 61 the cavity. The four blocked nucleotide feed stocks 63 are added to the vessel either by four separate pumps (not shown) or by a single pump with a valve controlling connection of the feed stock to the pump (not shown). At least one enzyme feed stock 64 can be added in the same manner. A computer (not shown) controls the sequential addition of blocked nucleotides and enzyme(s) to the vessel and controls the temperature of the solution.

Additional components could enhance the performance of the bulk scale synthesizer. Ancillary feed stocks 65 for additional blocked nucleotides, enzymes, or other reagents can be added. The temperature of the reaction solution is monitored by a temperature probe 55. A pH probe 56 monitors the reaction solution pH and acid or base feed stocks 62 can be added as necessary to maintain pH as desired. An inert gas such as nitrogen is slowly added via tube 57 to the reaction solution to remove oxygen (which can be monitored by an oxygen electrode). A computer (not shown) can control the apparatus, receiving inputs of solution temperature, pH, and sending outputs to control addition of feed stocks (blocked nucleotide feed stocks, enzyme feed stock(s), acid, base, and ancillary reagents), heating device, cooling valve 59, nitrogen purge rate, and motor rotation speed.

Maximizing product yield may require high concentration of reagents, e.g., 1.0–10 mM. The faster build-up of nucleoside and phosphate by-products may be reduced by adding a dialysis or ultrafiltration system to the apparatus. Alternatively, high phosphate levels may be reduced by precipitation out of solution by adding a cation that yields an insoluble phosphate salt, e.g., $Al^{3+}$, $Mg^{2+}$ or $Ca^{2+}$.

Reuse of nucleotide substrate, described by the method of the present invention, will reduce the cost of synthesizing an oligonucleotide by reducing the consumption of nucleotide substrate. The random probability is 25 percent that a base will be followed consecutively by the same base in an oligonucleotide. It follows that this technique can reduce the consumption of nucleotide substrate on average by 25 percent. This cost savings may be substantial, especially for bulk synthesis of oligonucleotides. By obviating the need to add nucleotide feed stock, the present invention may speed robotic automation. Thus, the present invention provides significant advantages for the routine use of oligonucleotide synthesis.

The method will now be further described by way of the following, non-limiting examples.

EXAMPLE 1

Synthesis of ApApCpApA using Basic Mode with Substrate Reuse

The oligonucleotide ApApCpApA was synthesized according to the following procedure. The following solution was placed in a total volume of 30 ul in an fependorf tube: 50 mM Tris-Cl, pH 8.0, 10 mM $MgCl_2$, 10 mM DTT, 0.1% TRITON X-100, 1 mM ApApC initial primer, and Nucleotide Substrate. The following procedure was performed:

Cycle 1

(a) Add 1 ul (20 units) T4 RNA Ligase (New England Biolabs), incubate at 37 degrees C. for 3 hours, heat at 85 degrees C. for 5 minutes, cool.

(b) Add 1 ul (3 units) T4 Polynucleotide Kinase (US Biochemicals, contains 3'-Phosphatase), incubate at 37 degrees C. for 1 hour, heat at 85 degrees C. for 5 minutes, cool.

Cycle 2—starting volume is 20 ul (a) same as cycle 1. No AppAp substrate was added. (b) same as cycle 1.

Sub-Example A: Nucleotide substrate was approximately 5 mM AppAp wherein the phosphate blocking group was the 3'-phosphate monoester. This preparation contained a small amount of 3',5'-ADP precursor to prevent covalent inactivation of RNA Ligase by adenylylation. Nucleotide substrate used in all examples was synthesized in this manner.

Sub-Example B: Nucleotide substrate was 5 mM 3',5'-ADP+ 4.5 mM ATP. These precursors are converted to AppAp in the first cycle by RNA Ligase. Supplementation with inorganic pyrophosphatase in a separate experiment improved oligonucleotide product yield.

Thin layer chromatography (TLC), using the SurePure Oligonucleotide Kit (US Biochemicals), confirmed the formation of ApApCpApA product for both sub-examples. TLC also confirmed that no significant inactivated nucleotide substrate AppA was formed for both sub-examples. Approximately 5 ul oligonucleotide product was incubated with 100 ng RNase A (US Biochemicals) at 37 degrees C. for about 15 minutes. RNase A is used as a base-specific RNase to cleave the oligonucleotide 3' to the Cytidine base. TLC confirmed the formation of ApA oligonucleotide product for both sub-examples. Yield of oligonucleotide product was better in sub-example A.

This experiment demonstrates reuse in the second cycle of nucleotide substrate AppAp used in the first cycle. This was accomplished by using bacteriophage T4 3'-Phosphatase under carefully controlled conditions to specifically remove the extended primer blocking group without significantly inactivating the nucleotide substrate AppAp. The high concentration of primer and nucleotide substrate used in this example and the following examples is for the convenience of allowing detection of product by TLC. Proportionately lower concentrations, such as 0.10 mM primer and 1.0 mM nucleotide substrate may be more appropriate for long oligonucleotides to lessen the build up of side products.

EXAMPLE 2

Synthesis of ApApCpApA Using Rye Grass 3'-Phosphatase

ApApCpApA was synthesized using the same procedure as example 1A, except 0.05 units 3'-Phosphatase from Rye Grass (Sigma, sold as 3'-Nucleotidase) was used for 3 hours at 37 degrees C. in place of T4 Polynucleotide Kinase (3'-Phosphatase). TLC confirmed synthesis of product and RNase A digestion confirmed formation of ApA.

EXAMPLE 3

Synthesis of ApApCpApA Using Preferred Mode with Substrate Reuse

The following solution was placed in a total volume of 30 ul in an ependorf tube: 50 mM Tris-Cl, pH 8.0, 10 mM $MgCl_2$, 10 mM DTT, 0.1% Triton X-100, 1 mM ApApC initial primer, and 5 mM AppAp. The following procedure was performed:

Cycle 1

(a) Add 1 ul (20 units) T4 RNA Ligase (New England Biolabs) 0.5 ul (0.025 units) 5'-Nucleotidase (Sigma), incubate at 37 degrees C. for 1 hour, heat at 85 degrees C. for 5 minutes, cool. The heat inactivation at this stage is optional.

(b) Add Exonuclease—see details below. Heat at 95 degrees C. for 5 minutes, cool.

(c) Add 0.5 ul (15 units) T4 Polynucleotide Kinase (US Biochemicals), incubate at 37 degrees C. for 30 minutes, heat at 85 degrees C. for 5 minutes, cool.

Cycle 2—starting volume is 20 ul (a) same as cycle 1, but incubation is extended to 135 minutes. No AppAp substrate was added.

(b) same as cycle 1.

(c) same as cycle 1.

Sub-Example A: Exonuclease added was 1 ul (0.02 units) Phosphodiesterase I (US Biochemicals). In this subexample only, 1 ul 100 mM ATP is added during RNA Ligase incubation in the second cycle to reform the substrate AppAp from 3',5'-ADP.

Sub-Example B: Exonuclease added was 1 ul (10 units) Exonuclease I (US Biochemicals)

Sub-Example C: Exonuclease added was 1 ul (0.1 units) Polynucleotide Phosphorylase (Sigma). In this subexample only, 0.2 mM $Na_2AsO_4$ was incorporated in the buffer throughout the synthesis to facilitate Polynucleotide Phosphorylase digestion of unextended primer chains.

TLC confirmed the formation of ApApCpApA product in all subexamples. Digestion with RNase A confirmed the formation of ApA in all sub-examples.

EXAMPLE 4

Synthesis of ApApCpApA Using Substrate Reuse, and AMP Inactivating Enzyme(s)

The following solution was placed in a total volume of 30 ul in an ependorf tube: 50 mM Tris-Cl, pH 8.0, 10 mM $MgCl_2$, 10 mM DTT, 0.1% Triton X-100, 1 mM ApApC initial primer, and 5 mM AppAp. The following procedure was performed:

Cycle 1

(a) Add 1 ul (20 units) T4 RNA Ligase (New England Biolabs) AMP Inactivating Enzyme(s), incubate at 37 degrees C. for 3 hours, heat at 85 degrees C. for 5 minutes, cool.

(b) Add 1 ul (3 units) T4 Polynucleotide Kinase (US Biochemical), incubate at 37 degrees C. for 1 hour, heat at 85 degrees C. for 5 minutes, cool.

Cycle 2

(a) same as cycle 1. No AppAp substrate is added.

(b) same as cycle 1.

Sub-Example A: AMP Inactivating Enzyme was 0.5 ul (0.025 units) 5'-Nucleotidase (Sigma)

Sub-Example B: AMP Inactivating Enzyme was 0.5 ul (0.025 units) 5'-Nucleotidase (Sigma)+1 ul (0.018 units) Adenosine Deaminase (Sigma).

Sub-Example C: AMP Inactivating Enzyme was 1 ul (0.004 units) AMP Deaminase (Sigma).

Sub-Example D: AMP Inactivating Enzyme was 1 ul (0.12 units) AMP Nucleosidase (*E. coli*).

TLC confirmed the formation of ApApCpApA product in all subexamples. TLC also confirmed that the AMP Inactivating Enzymes in all sub-examples converted substantially all substrate to product. In all sub-examples, TLC confirmed that the oligonucleotide ApA was cleaved from the product by RNase A digestion. It was also found that Adenosine Deaminase was not inactivated by heating at 95 degrees C., a useful property.

EXAMPLE 5

Synthesis of ApApCpApApdA Using Cycles With and Without Substrate Reuse

The following solution was placed in a total volume of 30 ul in an ependorf tube: 50 mM Tris-Cl, pH 8.0, 10 mM MgCl$_2$, 10 mM DTT, 0.1% Triton X-100, 1 mM ApApC initial primer, and 5 mM AppAp. The following procedure was performed:

Cycle 1: Reuse (a) add 1 ul (20 units) T4 RNA Ligase (New England Biolabs), incubate at 37 degrees C. for 1 hour, heat at 85 degrees C. for 5 minutes, cool.

(b) add 1 ul (3 units) T4 Polynucleotide Kinase (US Biochemicals), incubate at 37 degrees C. for 1 hour, heat at 85 degrees C. for 5 minutes, cool.

Cycle 2: No Reuse (a) add 1 ul (20 units) T4 RNA Ligase (New England Biolabs), incubate at 37 degrees C. for 1 hour, heat at 85 degrees C. for 5 minutes, cool.

(b) add 1 ul (0.035 units) Nucleotide Pyrophosphatase (Sigma, snake venom), incubate at 37 degrees C. for 30 minutes, heat at 95 degrees C. for 5 minutes, cool.

(c) add 1 ul (1.6 units) Alkaline Phosphatase (US Biochemicals, calf intestine), incubate at 45 degrees C. for 30 minutes, heat at 95 degrees C. for 5 minutes, cool. (Alkaline Phosphatases generally have better activity at higher temperatures, such as 45–60 degrees C.).

Cycle 3: No Reuse (a) add 2 ul (40 units) T4 RNA Ligase (New England Biolabs) 10 ul 10 mM AppdAp, incubate at 37 degrees C. for 80 minutes, heat at 85 degrees C. for 5 minutes, cool.

(b) same as cycle 2.

(c) same as cycle 2.

TLC strongly suggested formation of ApApCpApApdA product. Matrix assisted laser desorption mass spectroscopy confirmed formation of this product. Incubation of 5 ul oligonucleotide product with 100 ng RNase A (US Biochemicals) at 37 degrees C. for 15 minutes resulted in the cleavage of the oligonucleotide to ApApdA product as strongly suggested by TLC.

I claim:

1. A method for synthesizing a repeat region of an oligonucleotide having a defined sequence, said repeat region including a repeated nucleotide that appears more than once in succession, comprising the steps of:

(a) enzymatically coupling an oligonucleotide primer with a 3'-phosphate-blocked repeated nucleotide to form a 3'-phosphate blocked primer;

(b) removing the 3'-phosphate blocking group from the 3'-phosphate-blocked primer using a 3'-phosphatase enzyme substantially without removing the 3'-phosphate blocking group from unreacted 3'-phosphate-blocked repeated nucleotide; and (c) repeating steps (a) and (b) using unreacted 3'-phosphate-blocked repeated nucleotide from step (b) as the 3'-phosphate-blocked repeated nucleotide of step (a) and the deblocked primer product of step (b) as the oligonucleotide primer of step (a) without prior separation of the unreacted 3'-phosphate-blocked repeated nucleotide from the deblocked primer product.

2. A method according to claim 1, wherein the 3'-phosphatase is derived from bacteriophage T4.

3. A method according to claim 1, wherein the 3'-phosphatase enzyme is derived from rye grass.

4. A method according to claim 1, wherein the 3'-phosphate blocked repeated nucleotide is coupled to the oligonucleotide primer using RNA Ligase.

5. A method according to claim 4 wherein the 3'-phosphatase is derived from bacteriophage T4.

6. A method according to claim 4, wherein the 3'-phosphatase enzyme is derived from rye grass.

7. A method according to claim 4, wherein the 3'-phosphate-blocked repeated nucleotide has the general formula AppNp, wherein App is an adenosine diphosphate moiety which is released as adenosine monophosphate upon extension of the primer, and Np is a 3'-phosphate-blocked nucleoside moiety.

8. A method according to claim 7, wherein the 3'-phosphate-blocked nucleoside moiety is nucleosidyl-3'-phosphate monoester.

9. A method according to claim 7, further comprising the step of converting the adenosine monophosphate to a less reactive form, whereby any inhibitory effects of the adenosine monophosphate on the primer coupling reactions are reduced.

10. A method according to claim 7, wherein the 3'-phosphatase is derived from bacteriophage T4.

11. A method according to claim 7, wherein the 3'-phosphatase enzyme is derived from rye grass.

12. A method according to claim 1, wherein a single reaction cycle of steps (a) and (b) comprises the steps of incubating an oligonucleotide primer with RNA Ligase and AppNp or precursors thereof to form the extended primer;

heat inactivating the RNA Ligase;

incubating the heat-inactivated composition with 3'-Phosphatase to remove the phosphate blocking group from the 3'-end of the extended primer; and heat inactivating the 3'-Phosphatase, wherein App is an adenosine diphosphate moiety which is released as adenosine monophosphate upon extension of the primer, and Np is a 3'-phosphate-blocked nucleoside moiety.

13. A method according to claim 1, further comprising the step of adding an exonuclease to the composition prior to incubation with 3'-phosphatase.

14. A method according to claim 13, wherein the exonuclease is polynucleotide phosphorylase.

15. A method for synthesizing an oligonucleotide having a defined sequence including at least one repeat region in which a repeated nucleotide appears more than once in succession and at least one non-repeating region, wherein at least one non-repeating region of the oligonucleotide is synthesized by reaction cycles comprising the steps of extending a primer with a 3'-blocked nucleotide substrate to form an extended primer having a blocking group at the 3'-end;

inactivating unreacted 3'-blocked nucleotide substrate to render it less reactive than blocked nucleotide as a substrate for the primer extension reaction of step (a); and removing the blocking group from the extended primer to render it available for subsequent reaction cycles; and at least one repeat region is synthesized by reaction cycles comprising the steps of enzymatically coupling an oligonucleotide primer with a 3'-phosphateblocked repeated nucleotide to form a 3'-phosphate blocked primer; and removing the 3'-blocking group from the 3'-phosphate-blocked primer using a 3'-phosphatase enzyme substantially without removing the 3'-phosphate blocking group from unreacted 3'-phosphate-blocked repeated nucleotide; wherein unfeacted 3'-phosphate blocked repeated nucleotide from a first cycle is utilized as substrate in at least one successive cycle without prior separation from the primer from which the 3'-phosphate blocking group has been removed.

16. A method according to claim 15, wherein the 3'-phosphatase in derived from bacteriophage T4.

17. A method according to claim 15, wherein the 3'-phosphatase is derived from rye grass.

18. A method according to claim 16, wherein the primer is extended by enzymatically coupling substrate to the primer using RNA Ligase.

19. A method for synthesizing a repeat region of an oligoribonucleotide having a defined sequence, said repeat region including a repeated ribonucleotide that appears more than once in succession, comprising the steps of:

(a) enzymatically coupling an oligonucleotide primer with a 3'-phosphate-blocked repeated ribonucleotide to form a 3'-phosphate blocked primer;

(b) removing the 3'-phosphate blocking group from the 3'-phosphate-blocked primer using a 3'-phosphatase enzyme substantially without removing the 3'-phosphate blocking group from unreacted 3'-phosphate-blocked repeated ribonucleotide; and (c) repeating steps (a) and (b) using unreacted 3'-phosphate-blocked repeated ribonucleotide from step (b) as the 3'-phosphate-blocked repeated ribonucleotide of step (a) and the deblocked primer product of step (b) as the oligonucleotide primer of step (a) without prior separation of the unreacted 3'-phosphate-blocked repeated ribonucleotide from the deblocked primer product.

20. A method according to claim 19, wherein the oligonucleotide primer is coupled with a 3'-phosphate-blocked repeated ribonucleotide using RNA Ligase and the 3'-phosphatase is derived from bacteriophage T4.

21. A method according to claim 19, wherein the oligonucleotide primer is coupled with a 3'-phosphate-blocked repeated ribonucleotide using RNA Ligase and the 3'-phosphatase is derived from rye grass.

* * * * *